United States Patent [19]

Mieville

[11] Patent Number: 5,276,237

[45] Date of Patent: Jan. 4, 1994

[54] MEMBRANE AND USE THEREOF IN OXIDATIVE CONVERSION

[75] Inventor: Rodney L. Mieville, Glen Ellyn, Ill.

[73] Assignee: Amoco Corporation, Chicago, Ill.

[21] Appl. No.: 811,001

[22] Filed: Dec. 20, 1991

[51] Int. Cl.$^5$ .............................................. C07C 2/00
[52] U.S. Cl. ............................... 585/500; 585/654; 585/656; 585/658; 585/661; 585/700; 585/733; 585/943; 423/651; 423/418.2
[58] Field of Search .......... 585/500, 654, 656, 658, 585/661, 700, 733, 943; 423/415

[56] References Cited

U.S. PATENT DOCUMENTS

| | | | |
|---|---|---|---|
| 4,791,079 | 12/1988 | Hazbun | 502/340 |
| 4,822,944 | 4/1989 | Brazdil, Jr. et al. | 585/500 |
| 4,827,071 | 5/1989 | Hazbun | 585/500 |
| 5,012,028 | 4/1991 | Gupta et al. | 585/500 |

*Primary Examiner*—Patrick P. Garvin
*Assistant Examiner*—E. D. Irzinski
*Attorney, Agent, or Firm*—Scott P. McDonald; Richard A. Kretchmer; Frank J. Sroka

[57] ABSTRACT

A membrane of an oxidative conversion contact material of a mixed oxide of aluminum and at least one multivalent activator metal with the membrane permitting selective conveyance of a form of oxygen therethrough, as well as methods for the oxidative conversion of a gaseous hydrocarbon reactant using such membranes are provided.

24 Claims, 1 Drawing Sheet

MEMBRANE AND USE THEREOF IN OXIDATIVE CONVERSION

BACKGROUND OF THE INVENTION

This invention relates generally to membranes and their use and, more particularly, to oxidative conversion membranes which permit the selective conveyance of a form of oxygen therethrough and which membranes promote oxidative conversion reactions.

Natural gas is a primary chemical feedstock used in the manufacture of numerous chemicals, such as methanol, ammonia, acetic acid, acetic anhydride, formic acid, and formaldehyde, for example. Furthermore, as the uncertain nature of the limited supplies of and access to crude oil has become increasingly apparent, alternative sources of hydrocarbons and fuels have been sought out and explored. The conversion of low molecular weight alkanes (lower alkanes) to higher molecular weight hydrocarbons has received increasing consideration as such low molecular weight alkanes may be generally available from more readily secured and reliable sources. Natural gas, partially as a result of its comparative abundance, has received a large measure of the attention that has focused on sources of low molecular weight alkanes. Large deposits of natural gas, mainly composed of methane, are found in many locations throughout the world. In addition, low molecular weight alkanes are generally present in coal deposits and may be formed during numerous mining operations, in various petroleum processes, and in the above- or below-ground gasification or liquefaction of coal, tar sands, oil shale and biomass, for example.

Today, much of the readily accessible natural gas generally has a high valued use as a fuel whether in residential, commercial or in industrial applications. Additional natural gas resources, however, are prevalent in many remote regions of the world, such as remote areas of Western Canada, Africa, Australia, USSR and Asia. Commonly, natural gas from these remote resources is referred to as "remote natural gas" or, more briefly, "remote gas".

In many such remote regions, the widespread, direct use of natural gas as a fuel is generally not currently profitable or economical. Further, the relative inaccessibility of natural gas from such resources is a major obstacle to the more effective and extensive use of such remote gas as the transportation of the remote gas to distant markets wherein it could find direct use as a fuel is typically economically unattractive.

The dominant technology currently employed for the utilization of remote natural gas involves conversion of natural gas to a liquid form via the formation of synthesis gas, i.e., a process intermediary composed of a mixture of carbon monoxide and molecular hydrogen, generally having a hydrogen to carbon monoxide molar ratio in the range of about 1:5 to about 5:1 and commonly referred to as "syngas". Synthesis gas has utility as a feedstock for conversion to alcohols, olefins, or saturated hydrocarbons (paraffins) according to the well-known Fischer-Tropsch process, and by other means. When hydrocarbon products such as gasoline and diesel fuel are sought, the syngas can be converted to syncrude, such as with Fischer-Tropsch technology, and then upgraded to the desired transportation fuels using typical refining methods. Alternatively, syngas can be converted to liquid oxygenates which can be blended with conventional transportation fuels to form materials such as gasohol, used as an alternative fuel or converted to transportation fuels by catalyst such as certain zeolites.

Synthesis gas is not a commodity; rather, it is typically generated on-site for further processing.

Prior methods for producing synthesis gas from natural gas (typically referred to as "natural gas reforming") can be categorized as:

a) those relying on steam reforming wherein natural gas is reacted at high temperature with steam and wherein the heat required for the reforming is supplied externally;

b) those relying on partial oxidation in which methane is partially oxidized with pure oxygen by catalytic or non-catalytic means and wherein the heat for the process is supplied via the partial combustion of the feed; and c) combined cycle reforming consisting of both steam reforming and partial oxidation steps.

Steam reforming involves the high temperature reaction of methane and steam over a catalyst to produce carbon monoxide and hydrogen. As the catalyst used in steam reforming can be very sensitive to the presence of impurities such as sulfur, the feed typically is appropriately pretreated to remove such impurities, e.g., such as by hydrodesulfurization.

While steam reforming produces a product containing lesser amounts of coke, the syngas produced typically has a high ratio of hydrogen to carbon monoxide ($H_2/CO$), usually in excess of 3:1. Also, steam reforming processing generally suffers due to the relatively large inputs of energy required to conduct the highly endothermic methane steam reforming reaction. In addition, the use and presence of steam in such reforming typically necessitates the use of costly special alloys for construction of the reaction vessel.

In partial oxidation processing, the large amounts of heat required in reforming processing of natural gas is advantageously supplied by the partial combustion of feed material. Such processing, however, generally suffers as, in addition to the desired products of carbon monoxide and molecular hydrogen, substantial undesired coproduction of carbon dioxide and/or carbon also occurs. In addition, such processing requires the use of pure oxygen typically obtained by the separation of air, such as through a cryogenic separation, a relatively expensive process.

In combined cycle reforming processing, an expensive air separation step is also typically required, although such processes can result in some capital savings since the size of the steam reforming reactor is reduced in comparison to a standard steam reforming process.

Thus, it is desirable to facilitate and lower the cost of syngas production as by, for example, reducing the cost of the oxygen plant, such as by reducing the cost of separating and obtaining oxygen from air. A process and a means whereby oxygen or another form of oxygen can be obtained from a relatively low cost source, such as air, and without incurring the relatively high costs associated with conventional oxygen separation techniques has been sought and is desired.

Another oxidative conversion process is commonly referred to as "oxidative coupling". Oxidative coupling has been recognized as a promising approach to the problem of effectively converting lower alkanes to higher molecular weight hydrocarbons. A mechanism of action of oxidative coupling processing, however, has not been clearly identified or defined and is not clearly understood. In oxidative coupling processing, a low molecular weight alkane, such as methane, or a mixture containing low molecular weight alkanes, such as natural gas, is contacted with a solid material referred to by various terms including contact material, catalyst, promoter, oxidative synthesizing agent or activator. In such processing, the methane is contacted with the solid material and, depending on the composition of the material, in the presence or absence of free oxygen gas, and is directly converted to ethane, ethylene, higher hydrocarbons and water. Carbon dioxide, the formation of which is highly favored thermodynamically, is an undesired product, however, as the formation of carbon dioxide results in both oxygen and carbon being consumed without production of the desired higher value $C_{2+}$ hydrocarbons.

In such processing, catalytic mixtures containing reducible metal oxides are highly active but many such catalytic mixtures are undesirably very highly selective for producing $CO_2$, that is, they are combustion catalysts. In order to obtain desired selectivity for hydrocarbon formation, Group IA metals, particularly lithium and sodium, have been used in the catalytic mixtures. Under the conditions used for oxidative coupling processing, however, migration and loss of the alkali metal typically occurs. Furthermore, in order to avoid complete combustion processing of the feed, many methods for such oxidative conversion have been carried out in the absence of oxygen-containing gas, relying on the oxygen theoretically being supplied by the catalyst (e.g., lattice oxygen). Nevertheless, in most cases involving oxidative coupling processing of methane, carbon monoxide and hydrogen are coproduced in addition to desired $C_{2+}$ hydrocarbons.

Over the years, various additional oxidative coupling catalyst, contact agent, contact solid or the like compositions; additives, promoters, or the like for addition thereto and processes for oxidative coupling of hydrocarbons, particularly low molecular weight hydrocarbons such as methane, have been tested, reported or disclosed with varying degrees of success. Typifying these materials are those found in U.S. Pat. Nos. 4,444,984; 4,533,780; 4,547,607; 4,554,395; 4,567,307; and 4,568,785.

More particularly, U.S. Pat. Nos. 4,489,215; 4,495,374; 4,499,322; 4,499,323; 4,499,324; 4,450,310; 4,523,049; 4,656,155; 4,721,828; and 4,727,212 disclose processes utilizing compositions which, in addition to requiring, as a key component, a reducible metal oxide and/or depend on the utilization of lattice oxygen, include an alkali metal, an alkaline earth metal or combinations thereof.

For example, U.S. Pat. No. 4,495,374 discloses the use of a reducible metal oxide promoted by an alkaline earth metal in such a method of methane conversion. During such processing, the reducible metal oxide of the promoted oxidative synthesizing agent is reduced. The reduced synthesizing agent can then be removed to a separate zone wherein it is contacted with an oxygen-containing gas to regenerate the promoted oxidative synthesizing agent.

U.S. Pat. No. 4,523,049 shows a reducible metal oxide catalyst promoted by an alkali or alkaline earth metal, and requires the presence of oxygen during the oxidative coupling reaction. U.S. Pat. No. 4,656,155 specifies a reducible metal oxide in combination with an oxide of zirconium, an oxide of yttrium and, optionally, an alkali metal. U.S. Pat. No. 4,450,310 is directed to coupling promoted by alkaline earth metal oxides in the total absence of molecular oxygen. U.S. Pat. No. 4,482,644 teaches a barium-containing oxygen-deficient catalyst with a perovskite structure.

In addition, reference is made to the following commonly assigned U.S. patents concerned with the conversion of lower alkanes to higher molecular weight hydrocarbons via oxidative coupling/conversion:
1. U.S. Pat. Nos. 4,814,539 and 4,968,655 which disclose catalyst compositions containing a reducible compound on a silica-containing support;
2. U.S. Pat. Nos. 4,992,409 and 5,053,578 which disclose catalytic compositions including a Group IA metal, a Group IIA metal and a third component, the precursor of which is a sol such as an aqueous suspension of a metal such as aluminum, silicon, titanium, zinc, zirconium, cadmium or tin with which the other components of the composition are thoroughly dispersed; and
3. U.S. Pat. No. 5,028,577 which discloses a catalytic composition including a Group IA metal, a Group II metal, a third component the precursor of which comprises a sol (an aqueous suspension of aluminum, silicon, titanium, zinc, zirconium, cadmium or tin) and a fourth component including a Group VIII metal, silver or a combination thereof.

In addition, commonly assigned U.S. Pat. Nos. 4,751,336; 4,754,336; 4,754,091 and 4,754,093 disclose oxidative coupling of lower molecular weight alkanes to higher molecular weight hydrocarbons utilizing a catalyst comprising silica free of a reducible metal oxide.

Several patents describe catalysts for higher hydrocarbon synthesis which can include a Group IIA metal; a metal of scandium, yttrium or lanthanum; and/or other metal oxides.

For example, U.S. Pat. No. 4,780,449 discloses a catalyst including metal oxides of a Group IIA metal, a Group IIIA metal, a lanthanide series metal excluding Ce, or mixtures thereof. The patent lists as optional promoter materials metal oxides of a metal of Groups IA, IIA, IIIA, IVB, VB, IB, the lanthanide series, or mixtures thereof.

Reference is also made to the following commonly assigned patents:
1. U.S. Pat. Nos. 4,939,311 and 5,024,984 which relate to a catalyst composition comprising a mixed oxide of:
  a) a Group IIIB metal selected from the group consisting of yttrium, scandium and lanthanum;
  b) a Group IIA metal selected from the group consisting of barium, calcium and strontium; and
  c) a Group IVA metal selected from the group consisting of tin, lead and germanium, with the Group IIIB, Group IIA and Group IVA metals in an approximate mole ratio of 1:0.5–3:2–4, respectively, and a process employing same; and
2. U.S. Pat. Nos. 4,971,940 and 5,059,740 relating to a tin-containing composition and use, the composition comprising oxidized tin and having a specified tin Auger line transition.

Reference is also made to commonly assigned patent application U.S. Ser. No. 775,209 which discloses a contact material containing an intimately mixed, mixed oxide of at least one cationic species of a naturally occurring Group IIIB element, at least one cationic species of a Group IIA metal of magnesium, calcium, strontium, and barium and a cationic species of aluminum, as well as methods of hydrocarbon conversion using such contact material compositions.

The conversion of methane to higher molecular weight hydrocarbons in the presence of such solids, as described in the above patents, takes place at elevated temperatures in the range of about 500° C. to 1,200° C. The reaction is strongly exothermic in nature and in order to properly regulate the reaction and to prevent the occurrence of excessive undesirable side reactions, it is necessary to remove exothermic heat of reaction, avoiding an excessive temperature rise and lowering the temperature of the reaction product stream.

Fluidized bed reactor systems have been considered for the conversion of methane to higher molecular weight hydrocarbons. Fluidized bed reactor systems, however, generally suffer from problems of gas and solids back-mixing and gas bypassing with resulting losses in selectivity and yield. In addition, due to the high temperatures typically encountered in such processing and the large amounts of heat generated during such exothermic conversions, the physical structure of the reactor itself can be critical.

Problems particular to this conversion of methane include the fact that the reaction temperature is high enough to preclude or bring into serious question the use of many materials commonly used in reactor construction.

In recent years, workers in the field have proposed various reactor and processing configurations including some that make use of ceramic membranes.

For example, U.S. Pat. Nos. 4,791,079 and 4,827,071 disclose a multilayer membrane for use in hydrocarbon conversion, such as hydrocarbon oxidation and/or dehydrogenation processing. The multilayered membrane of these patents includes one layer which is an impervious mixed ion and electron conducting ceramic such as yttria stabilized zirconia which is doped with sufficient $CeO_2$ or titanium dioxide to impart electron conducting characteristics to the ceramic. A second layer associated with the mixed ion conducting impervious ceramic is a porous ion conducting layer containing a selective hydrocarbon oxidation catalyst. These patents also disclose that in order to enhance oxygen dissociation, it may be desirable to further provide a thin layer of an oxide of lanthanum, chromium, tin, or the like on the surface of the membrane which contacts oxygen.

An oxygen-containing gas is contacted with the mixed ion and electron-conducting layer while a reactant such a hydrocarbon is contacted with the porous catalyst-containing layer with the system being maintained at reaction conditions. Oxygen ions pass through the mixed-conducting layer and catalytically react with the hydrocarbon in the porous catalyst containing layer. Product is separated from the porous layer while electrons pass through the mixed-conducting layer to balance the system.

U.S. Pat. No. 4,855,111 discloses a reactor with an annular reaction zone with ceramic baffles positioned therein perpendicular to the flow of a mixture of gas and fluidized solid catalyst. The baffles have openings adapted to permit passage of the gas solid mixture therethrough essentially only in the overall direction of flow from inlet to outlet. The patent states that known ceramic materials having sufficient strength at the elevated temperatures necessary for methane conversion can be employed. A ceramic material predominantly of alumina and which may contain minor amounts of oxides of silica, calcium and the like is disclosed as a preferred ceramic material.

U.S. Pat. No. 4,329,208 relates to the conversion of ethylene to ethylene oxide utilizing a solid electrolyte onto one surface of which is deposited an oxidation catalyst and onto a second surface of which is deposited a second catalyst capable of dissociating oxygen gas to oxygen ions. Oxygen ions are transported under a positive voltage applied through the solid electrolyte to react with ethylene to form ethylene oxide.

U.S. Pat. No. 4,599,157 relates to a selectively permeable composite membrane which permits oxygen gas to pass through while substantially blocking water vapor. In one embodiment, the selectively permeable composite membrane is a two-layer construction including a porous membrane layer having micropores and a thin layer containing, in a carbon matrix, a water-containable or wettable metallic oxide, a metal oxide having the capability of absorbing oxygen, or a metal oxide having a rutile-type crystal structure.

European Patent Application Publication No. 0 399 833 relates to a solid multicomponent membrane, electrochemical reactor and use of membranes and reactor for oxidation reactions. The membranes include substantially discrete phases of a) an electronically conductive material and b) an oxygen ion-conductive material and/or a mixed metal oxide having a perovskite structure. The electrochemical reactors are disclosed for use in a continuous process for transporting oxygen from an oxygen-containing gas to any reacting gas that consumes oxygen.

The electronically-conducting material or phase of the membrane is disclosed as being any material which exhibits sufficient electronic conductivity under the conditions of the reaction. Suitable metals and metal oxides for use in the electronically-conducting phase are disclosed as including silver, gold, platinum, rhodium, ruthenium, palladium, nickel, cobalt, copper, etc., among which palladium and platinum are preferred and bismuth oxides, tin-indium oxide mixtures, praeseodymium-indium oxide mixtures, cerium lanthanum oxide mixtures, niobium-titanium oxide mixtures, electron-conductive mixed metal oxides of a perovskite structure, etc., among which the metal-doped metal oxides are preferred.

The oxygen ion-conducting materials or phases of the dual-conductor are disclosed as typically being solid solutions formed between oxides containing divalent and trivalent cations such as calcium oxide, scandium oxide, yttrium oxide, lanthanum oxide, etc., with oxides containing tetravelent cations such as zirconia, thoria and ceria where the oxygen ion-conducting material or phases comprise an oxygen ion-conductive mixed metal oxide of a perovskite structure. Disclosed as preferred among the solid electrolytes are the $Y_2O_3$-(yttria) and CaO-(calcia) stabilized $ZrO_2$-(zirconia) materials. Also, a wide variety of elements and oxides of elements are disclosed for use in forming perovskites useful in the invention thereof. Disclosed as examples of preferred elements are "La, Co, Sr, Ca, Fe, Cu, Ni, Mn, Or[sic], Y, Ba, Ti, Ce, Al, Sm, Pr, Nd, V, Gd, Ru, Pb, Na, W, Sc, Hf, Zr, oxides thereof, and mixtures thereof".

The document further discloses that the electrochemical cell may optionally contain a catalyst adjacent to or coated on the first conductive surface.

Also, Otsuka et al. in "Catalytic Activity and Selectivity Control for Oxidative Coupling of Methane by Oxygen Pumping Through Yttria Stabilized Zirconia,"

*Chemistry Letters*, pp. 319–322 (1985) describe the oxidative coupling of methane using electrochemically pumped oxygen through yttria stabilized zirconia having silver coated on one surface and silver-bismuth oxide coated on the other surface. In each case, the silver acted as an electrode which was necessary to complete the circuit external of the membrane and thus to permit the desired reaction to proceed. Otsuka et al. teach that the oxidative coupling of methane took place only when the circuit was closed by connection of lead wires from both electrodes.

Michaels et al. in "Kinetics of Vapor—Phase Electrochemical Oxidative Dehydrogenation of Ethylbenzene," *Journal of Catalysis*, 85, pp. 477–487 (1984) describe electrochemical oxidative dehydrogenation of ethylbenzene to styrene using an yttria stabilized zirconia ionic conductor in the form of a tube with porous platinum electrodes deposited in both inner and outer surfaces which are connected via an external circuit.

Stoukides et al. in, "The Effect of Electrochemical Oxygen Pumping on the Rate and Selectivity of Ethylene Oxidation on Polycrystalline Silver," *Journal of Catalysis*, 70, pp. 137–146 (1981) describe electrochemical oxidation of ethylene using an yttria stabilized zirconia ionic conductor having a porous silver catalyst film on both surfaces which films function as electrodes and are connected via an external circuit.

An important problem in many of the systems described above is the necessary provision of a catalyst layer deposited on the impervious ion conducting material which layer serves both as catalyst and as external electrode. It is difficult to secure such electrodes to surfaces of the ceramic membrane and to maintain the integrity of the electrode-membrane bond during sustained use at the severe conditions normally encountered. Without such electrodes connected externally, however, the desired electrochemical reaction did not proceed.

Thus, a membrane material which allows for the transport or conveyance of oxygen or a form of oxygen without requiring the attachment of an external electrode with the application of an electronic or electric potential to the membrane is desired. Further, in view of the problems associated with fabrication of membrane structures for the selective transport of oxygen, particularly those structures which contain a catalyst or the like to promote the desired oxidative conversion reaction, a membrane:
1. which is capable of promoting oxidative conversion reactions without requiring the addition of a catalyst layer onto the membrane and/or
2. comprises a material with which the catalyst of such additional catalyst layer is compatible to facilitate manufacture, is desired.

SUMMARY OF THE INVENTION

A general object of this invention is to provide an improved membrane and membrane structure and an improved process for the oxidative conversion of a gaseous hydrocarbon reactant.

A more specific objective of the present invention is to overcome one or more of the problems described above.

The prior art fails to disclose or suggest membranes of oxidative conversion contact material which are substantially impervious to non-oxygen gas and which additionally permit the selective conveyance of a form of oxygen therethrough. The membranes of the invention, as well as the membrane structures of the invention which contain such membranes and the methods of oxidative conversion of hydrocarbon reactants in which such membranes are used, by being able to convey a form of oxygen without requiring the application of electrodes and an electric potential can simplify construction and operation of the membranes. Further, such membranes and the use thereof can significantly reduce processing costs reducing the cost of oxygen which by means of the invention can be obtained, such as from air, in a relatively cost efficient manner. Such membranes and the use thereof can also facilitate heat removal, thereby assisting in temperature control during highly exothermic reaction processing.

The general object of this invention can be attained, at least in part, through a membrane structure having a membrane of an oxidative conversion contact material of a mixed oxide including a cationic species of aluminum and a cationic species of at least one multivalent activator metal. The membrane permits the selective conveyance of a form of oxygen therethrough.

The invention further comprehends a membrane structure having a membrane, substantially impervious to non-oxygen gases, containing an oxidative conversion contact material of a mixed oxide including a cationic species of aluminum and a cationic species of at least one multivalent activator metal. The membrane forms a first and a second surface and permits the selective conveyance of a form of oxygen therethrough from the first surface towards the second surface. The first surface of the membrane additionally includes an oxygen dissociation catalyst effective in facilitating the dissociation of oxygen.

The invention still further comprehends a membrane structure having a membrane, substantially impervious to non-oxygen gases, containing an oxidative conversion contact material of a mixed oxide including a cationic species of aluminum and cationic species of at least one multivalent activator metal of yttrium or barium. The membrane forms a first and a second surface and permits the selective conveyance of a form of oxygen therethrough from the first surface towards the second surface. The first surface of the membrane additionally includes an oxygen dissociation catalyst including at least one metal selected from the group of palladium and platinum and is effective in facilitating the dissociation of oxygen.

The invention also comprehends methods for the oxidative conversion of a gaseous hydrocarbon reactant. In such methods, a first surface of a specified membrane is contacted, at oxygen conveyance conditions, with an oxygen-containing gas. A second surface of the specified membrane is contacted, at reactive conditions and in the presence of a form of oxygen conveyed by the membrane, with at least one gaseous hydrocarbon reactant capable of reacting with oxygen to produce an oxidative conversion product.

The invention also comprehends methods for the oxidative conversion of methane wherein methane is a hydrocarbon reactant in the process.

The invention also comprehends such methods of oxidative conversion wherein an oxygen-containing gas including free oxygen, such as from air, for example, is utilized.

The phrase "membrane structure" as used herein is in reference to various structures, forms, configurations or the like which contain the membrane of the invention and which, as in specifically described embodiments, can also include other materials including, for example, oxygen dissociation catalysts and hydrocarbon oxidative conversion catalysts, as described later herein.

The phrase "substantially impervious to non-oxygen gas" as used herein in reference to the subject membranes is defined to mean that such a membrane does not permit a substantial amount of non-oxygen gas to pass through the membrane as a gas (i.e., the membrane is non-porous, rather than porous, with respect to non-oxygen gases). In some cases, a minor degree of perviousness to non-oxygen gases might be acceptable or unavoidable, such as when hydrogen gas is present.

The phrase "a form of oxygen" as used herein includes dioxygen (ion and molecule) and mono-oxygen (ion and radical), for example.

Other objects and advantages of the invention will be apparent to those skilled in the art when the following detailed description taken in conjunction with the appended claims.

DETAILED DESCRIPTION OF THE INVENTION

According to the invention, membrane structures and methods for the oxidative conversion of gaseous hydrocarbon reactants are provided.

The invention provides a membrane structure containing a membrane useful in continuous processing involving reactant gases and specifically hydrocarbon reactant gases that consume oxygen. Processes which may be conducted with the subject membrane structure include, for example:
a) the combustion of hydrogen to produce water;
b) partial oxidation processing such as the partial oxidation of:
  1. methane or natural gas to produce synthesis gas ($CO$ and $H_2$) or unsaturated compounds;
  2. hydrocarbons to form aldehydes, ketones, alcohols and acids (either alkyl or aromatic); and
c) oxidative coupling processing such as the oxidative coupling of:
  1. natural gas, methane or other lower alkanes to higher molecular weight hydrocarbons; and
  2. other hydrocarbons to form higher molecular weight hydrocarbons.

Figure 1A:
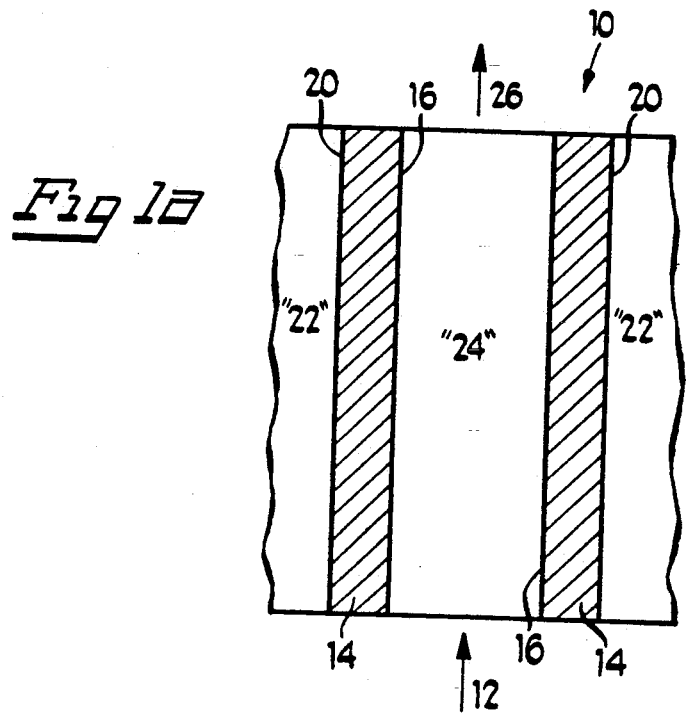
FIGS. 1a and 1b are simplified partial schematic cross-section depictions of a side and a top view, respectively, of one embodiment of the membrane structure of the invention.
Figure 1B:
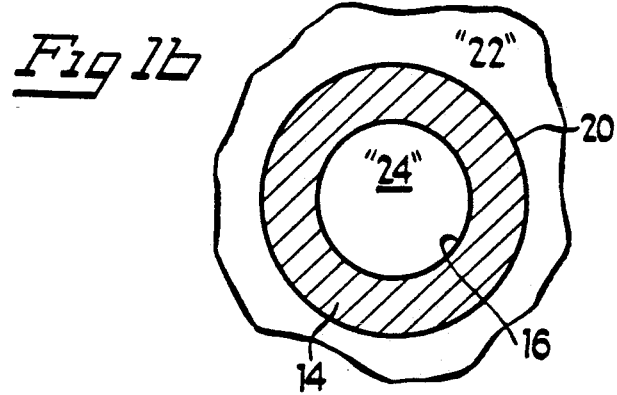

A relatively simple membrane structure, in accordance with the invention, which can readily be fabricated is a tubular membrane structure illustrated in FIGS. 1a and 1b. FIGS. 1a and 1b show a tubular membrane structure 10 wherein a reactant gas 12 is injected inside a membrane tube 14 contacting the inner surface 16 of the tube 14. The outer surface 20 of the membrane tube 14 is contacted with an oxygen-containing gas 22, such as air. It is to be understood that sources or forms of oxygen-containing gas other than air can be used or preferred in the practice of the invention. A form of oxygen is conveyed through the membrane structure 10 towards the inner surface 16 of the tubular membrane 14.

In the tube passageway "24" a gaseous mixture containing unreacted reactant as well as oxidative conversion products and which will vary in composition (both in components and concentrations) dependent on the selected processing operation is formed. For example, as identified above, partial oxidation processing of methane or natural gas can produce synthesis gas or unsaturated compounds, while oxidative coupling processing of natural gas, methane or other lower alkanes can result in the formation of higher molecular weight hydrocarbons.

A gaseous stream 26 exits from the membrane structure 10.

The membrane is substantially impervious to non-oxygen gases, i.e., those gases which contain molecules comprising elements other than oxygen such as hydrocarbon reactant gas of $CH_4$, for example, or $N_2$ as well as those which include oxygen atoms in the form of a gaseous compound. The membrane does, however, permit the conveyance of a form of oxygen via the membrane.

According to a preferred embodiment of the invention, the oxygen-containing gas contains at least about 1% free oxygen, i.e., molecular oxygen, and more preferably the oxygen-containing gas is air. Such free oxygen-containing gas can vary in molecular oxygen content from pure or substantially pure oxygen, to oxygen diluted with an inert gas such as, for example, nitrogen or argon, to a more complex gas mixture containing oxygen such as, for example, air, or air enriched with oxygen, or air diluted with a diluent (oxygen depleted air).

It is to be understood that in the practice of the invention, such free oxygen-containing gases can, if desired, be supplemented or replaced by an oxygen-containing gas which, for example, includes oxygen in the form of a gaseous compound such as steam or oxides of nitrogen such as $NO_x$ (where $x = \frac{1}{2}$, 1, 3/2 or 2, for example), or oxides of sulfur such as $SO_y$ (where $y = 2$ or 3, for example). If desired, such gaseous compounds of oxygen can be used in a substantially pure form, diluted with free oxygen or inert gases or in a more complex gas mixture which can include one or more of such gaseous oxygen-containing compounds, free oxygen, and inert gases, for example.

In any case, as the membrane structure of the invention reduces or, preferably, eliminates the need for a pretreatment step of oxygen separation, the invention is perceived as having particular utility with respect to oxygen-containing gases which in addition to free oxygen comprises at least one other gaseous component, such as air which in addition to free oxygen contains principally nitrogen gas as well as minor amounts of other gaseous components.

It is also to be understood that the above process can, of course, be reversed by having an oxygen-containing gas pass through the inner passage and an oxygen-consuming gas, e.g., hydrocarbon reactant gas, pass through the outer passage. Oxygen would then be conveyed through the membrane to the outside surface of the membrane.

In one preferred embodiment of the invention, the oxygen-containing gas which is contacted with the surface of the membrane tube (in the illustrated embodiment such surface is the outer surface "20" or the tube "14") is moved or flowed past such membrane surface at a selected rate thereby facilitating removal of heat generated during the exothermic oxidative conversion reactions. Further, as the oxygen concentration in the gas adjacent to this surface of the membrane is diminished as a form of oxygen is conveyed via the membrane, maintaining such movement or flow of the oxygen-containing gas adjacent such surface of the membrane contributes to maintaining the oxygen concentration at a level conducive to oxygen conveyance via a membrane. The selection of an appropriate rate and direction of flow of the oxygen-containing gas (e.g., whether such flow is parallel or perpendicular, or something therebetween relative to the membrane and whether such flow is countercurrent, cocurrent, neither or a variation thereof to the flow of oxygen-consuming gas on the other side of the membrane) can be determined by one skilled in the art and guided by the teachings herein.

The present invention provides a membrane containing an oxidative conversion contact material of a mixed oxide which may suitably comprise, consist of, or consist essentially of a cationic species of aluminum and a cationic species of at least one multivalent activator metal preferably having a relatively high alkalinity such as selected from Group 1, Group 2, Group 3, Group 13 or the rare earth elements of the Periodic Table of Elements. Basic oxides, such as those containing such selected cationic species, have been found to be generally superior in terms of yield and/or selectivity in the oxidative coupling processing of methane to higher molecular weight hydrocarbons, as compared to the use of acidic oxides in such processing, for example. As used herein, "Periodic Table of Elements" refers to the new notation version found on the inside front cover of the "Handbook of Chemistry and Physics", 70th Edition, published in 1989 by the Chemical Rubber Company. Specific metal components which can be used as activator metals include components of lithium, sodium, potassium, rubidium, magnesium, calcium, strontium, barium, scandium, yttrium, lanthanum, gallium, indium, thallium, cerium, praseodymium, neodymium, samarium and terbium, among which the Group 2 elements (Mg, Ca, Sr and Ba), Group 3 elements (Sc and Y), Ga, Ce and Pr are preferred. Of these, cationic species of Ba and Y have been found to be particularly useful in the practice of the invention.

The preferred mixed oxide is comprised predominantly of alumina and contains minor amounts of oxides of appropriate multivalent activator metals such as yttrium and barium. Such activator metals can be added to suitably improve one or more of:

a) the catalytic properties of the material in its use in oxidative processing, and
b) the mechanical and physical characteristics of the material in its use as a membrane including the oxygen transport characteristics of such membranes.

In the practice of the invention, such mixed oxides will generally contain at lease about 50 wt. % aluminum and usually about 50 to 90 wt. % aluminum and about 1 to 50 wt. % activator metal and preferably will contain at least about 50 to 70 wt. % aluminum and no more than about 1 to 30 wt. % activator metal. In one embodiment of the invention, activator metals such as Y and Ba were used in an amount of about 5 wt. %. (All such wt. %, as used herein, are in reference to the material on an oxygen-free basis.)

The membrane of the invention can be made by various means.

For example, the membrane of the invention can, if desired, be formed by a technique commonly referred to as "slip-casting". In general, in slip-casting, finely ground material in a liquid suspension, or slip, is poured into a porous mold which absorbs liquid and leaves a layer of the material deposited on the walls of the mold. When the desired thickness of the material is obtained in the mold, excess liquid is poured out. The deposited casting is then allowed to dry before being removed for sintering and annealing, to produce a mechanically stable form. A conventional mold material, such as plaster, can be used.

Alternatively, a method of preparation in accordance with common and well-known techniques such as tape casting, extrusion, or molding with a core such as by chemical vapor deposition or dip coating on a porous tube can, if desired, be utilized.

It is also to be understood that in a process utilizing the membrane structure of the invention, total conversion can be increased considerably by the selection of an appropriate design of the structure containing the membrane. For example, total conversion can be increased by the use of membrane structure composed of multiple tubes so as to increase the relative area of the membrane material exposed to the reactant relative to the volume ratio of the inner passage.

It is to be further understood that while the membrane structure of the invention as well as the process use thereof have been described above with reference to tubular structures, the invention is not so limited as the membrane can be fabricated into shapes or structures appropriate for various designs including, for example; baffles, and various manifold configurations such as a honeycomb structure, for example, whereby the surface area of the membrane is preferably increased relative to the flow rate of the reactant gas and/or the amount of oxygen conveyed through or by the membrane.

In one preferred embodiment of the invention, a tubular form of the membrane structure disclosed herein is utilized in the oxidative coupling/conversion of natural gas, methane or other lower alkane (typically $C_1$-$C_3$) to higher molecular weight hydrocarbons. In practice, such reactions typically occur at elevated temperatures in the range of about 500° C. to about 1,200° C., preferably in the ranges of about 600° C. to about 1,000° C. and, more preferably, in the range of from about 700° C. to about 900° C.

These temperature ranges have been found to be preferred as operation at temperatures below about 600° C. may generally result in the contact material of the membrane structure having relatively unfavorable product (e.g., $C_{2+}$ hydrocarbons) selectivities while operation at higher temperatures, e.g., temperatures significantly greater than about 900° C., can result in generally undesirable thermal reactions seriously competing with coupling reactions. The products resulting from such thermal reactions will typically be largely comprised of $H_2$, $CO_x$ (where x=1 or 2) and may also include coke, acetylene and aromatics such as benzene, for example. Such thermal reactions will typically overwhelm the desired coupling reactions when temperatures exceed about 1,000° C. It is to be understood, however, that at higher reaction temperatures at least trace quantities of aromatic compounds may also form.

However, in the oxidative coupling processing of lower alkanes, e.g., methane, the membrane of the invention can serve the dual function of conveying a form of oxygen as well as promoting the coupling reaction for the formation of higher molecular weight hydrocarbons. Since oxygen conveyance is generally favored by higher temperatures and as temperatures significantly greater than about 900° C. can result in generally undesirable thermal reactions seriously competing with the desired coupling reactions, it is generally preferred that such processing employing the subject membrane be done at a temperature at the higher end of about 700° C. to about 900° C. range, preferably at about 900° C.

By such an oxidative coupling/conversion process the feed hydrocarbon (e.g., methane) is converted to higher molecular weight hydrocarbons (e.g., ethane and ethylene), illustrative of saturated and unsaturated aliphatic hydrocarbon products having higher molecular weights than the feedstock alkane from which they were formed, and possibly some traces of aromatics or higher hydrocarbons, as well as some carbon dioxide, carbon monoxide and water.

In another preferred embodiment of the invention, a tube form of the membrane structure disclosed herein is utilized in the partial oxidation of methane or natural gas to produce synthesis gas. In practice, such processing is generally done at elevated temperatures, such as a temperature in the range of about 500° C. to about 1,200° C. and, preferably, in the range of 600° C. to about 1,000° C.

The synthesis gas produced by this process of the invention is substantially nitrogen-free even when utilizing air or similar nitrogen-containing as a source for oxygen. The product synthesis gas comprises a mixture of hydrogen and carbon monoxide, and may contain some minor amounts (typically less than 5 wt. % and generally no more than about 1 to 3 wt. %) of acetylene, ethylene or both. As identified above, the synthesis gas can be converted to liquids using a Fischer-Tropsch process or converted to methanol by commercial processes, for example, as desired.

In general, as the flux of a form of oxygen via the membrane is increased with higher temperatures, utilization of the membrane structure of the invention is currently preferred in those gas phase oxidative conversion processes occurring at temperatures greater than about 400° C. as at such higher temperatures a sufficient flux of oxygen via the membrane is obtained to make such processing of interest. In addition to processes such as the oxidative coupling of natural gas, methane or other lower alkanes to higher molecular weight hydrocarbons and the partial oxidation of methane or natural gas to produce synthesis gas or unsaturated compounds, identified above, other examples of such specific gas phase oxidation processes occurring at temperatures greater than about 400° C. include such oxidative processes as the production of:

a) maleic anhydride by the oxidation of hydrocarbons such as benzene or butene using a catalyst such as molybdenum oxide/vanadium oxide;

b) acetone by the oxidation of isopropanol using a catalyst such as a zinc oxide catalyst;

c) formaldehyde by the oxidation of methanol using a catalyst such as a silver based catalyst;

d) benzene carboxylic acid by the oxidation of methyl benzenes using a catalyst such as a vanadium oxide catalyst; and e) phthalicanhydride by the oxidation of naphthalene using a catalyst such as a vanadium oxide catalyst.

It is also to be understood that the membrane can also be used as a component in fuel cells, if desired.

The temperature at which the membrane is contacted with the oxygen-containing gas (i.e., the oxygen conveyance temperature) will generally be at most only a few degrees less than the conversion reaction temperature, as the thickness of the membrane structure is typically all that separates the oxygen-containing feed gas from reactant material.

In order to improve the performance of the membrane in oxidative conversion processing, in one preferred embodiment of the invention it is desirable to further provide an oxygen dissociation catalyst at the surface of the membrane which contacts the oxygen-containing gas. Useful oxygen dissociation catalysts include the Noble metals and mixtures thereof and which Nobel metals and mixtures thereof are in a stable form at the specified reaction conditions. Preferred Nobel metals include platinum and palladium, preferably in a metallic or zero valent form.

The use of such oxygen dissociation catalysts is generally advantageous in that they can help effect the dissociation of oxygen, that is such catalysts can be useful in effecting conveyance of a form of oxygen via the membrane.

In practice, it is preferred that such oxygen dissociation catalyst, if used, form a relatively thin discontinuous film on the surface of the membrane which contacts the oxygen-containing gas. The dissociation catalyst serves to facilitate or catalyze the dissociation of oxygen into a form to facilitate its conveyance via the membrane. As a continuous film on the membrane surface can act as a barrier, either physical or otherwise, to the conveyance of a form of oxygen via the membrane, the film of the oxygen dissociation catalyst is preferably discontinuous so as to provide locations for the contacting of the dissociated oxygen with the surface of the membrane. Further, as thick layers of material involve more material and are thus generally more costly, relatively thin films are desired, to the extent they can be physically applied and maintained. The film of oxygen dissociation catalyst will typically cover no more than about 50% of the membrane surface which contacts the oxygen-containing gas, with those portions of the membrane surface covered by such a discontinuous film being relatively well distributed among the total membrane surface. In general, when such dissociation catalysts are used, a relatively small amount of the oxygen dissociation catalyst material is believed needed to beneficially effect oxygen conveyance via the membrane of the invention. For example, when used, an amount of oxygen dissociation catalyst of at least about 0.1 monolayer, as measured for the external surface area of the membrane, can beneficially effect processing.

Such oxygen dissociation catalyst, if used, can be added to the membrane structure in any appropriate manner. For example, an aqueous solution containing the desired oxygen dissociation catalyst or a precursor thereof can be selectively brushed onto the desired membrane structure surface. As a more specific example, the oxygen dissociation catalyst, platinum, can be added to the membrane by appropriately brushing the desired membrane surface with a platinum-containing solution such as a solution of chloroplatinic acid and water, containing about 0.2 wt. % platinum.

It is to be understood that the membrane structure of the invention may optionally include an additional catalyst material adjacent to or coated on at least a portion of the surface of the membrane which contacts the hydrocarbon reactant. For example, if used in the oxidative coupling of hydrocarbons including the oxidative coupling of natural gas, methane or other lower alkanes to higher molecular weight hydrocarbons, catalyst or contact materials such as those described above, particularly those catalysts or contact materials which contain a form of Al as a significant component, e.g., a material typically containing at least about 2 to 20 wt. % aluminum (on an elemental basis). Examples of such materials include such Al-containing forms of the compositions identified in U.S. Pat. Nos. 4,992,409, 5,053,378 and 5,028,577 and especially those identified in U.S. Ser. No. 775,209 which materials can be so used in conjunction with the membrane and as a part of the membrane structure of the invention. Such Al-containing compositions are generally preferred as they are more generally more similar in composition to the membrane material and, as a result, are generally more readily adhered, fastened or bonded to the membrane.

As a further example, if used in syngas production, the membrane structure of the invention can preferably include a syngas production catalyst, such as those known in the art, adjacent to or on the surface of the membrane which contacts the hydrocarbon reactant. Again, those catalysts which comprise Al or a form thereof such as syngas production catalyst of Rh, Ru or Ni on $Al_2O_3$ will typically be preferred, for the same general reasons identified above relative to preferred oxidative coupling contact materials.

It is also to be understood that other catalyst materials can, if desired, be used in conjunction with the membrane, dependent upon the specific desired processing.

When used, such additional catalysts can be placed and secured to the membrane or as a part of the membrane structure in any appropriate manner. One preferred technique for the placement of such an additional catalyst is to coat or "paint" the specified membrane surface with a slurry of the specified catalyst or precursor thereof. Again, as with the use of oxygen dissociation catalysts, described above, it is preferred that, if used, such catalyst permits the transport of a form of oxygen, such as by the catalyst forming a relatively thin discontinuous film on the specified surface of the membrane or through the use of a sufficiently porous supported form of catalyst.

The membranes and the processes utilizing the subject membranes, illustratively disclosed herein, can suitably be practiced in the absence of any component or ingredient or process step, respectively, which is not specifically disclosed herein.

The present invention is described in further detail in connection with the following examples which illustrate various aspects involved in the practice of the invention. It is to be understood that all changes that come within the spirit of the invention are desired to be protected and thus the invention is not to be construed as limited by these examples.

EXAMPLES

EXAMPLE 1

Fabrication of membrane tube of 5% lanthanum oxide/alumina

A 1,000 gram batch of 5 wt. % lanthanum oxide/alumina material was prepared by weighing and dry mixing appropriate amounts of $La_2O_3$ and $Al_2O_3$ in a twin shell dry blender for thirty minutes. The mixed batch of material was then granulated in an Eirich mixer with 15% (based on weight of dry batch) distilled water added. The water-added material was allowed to mix for 10 minutes to form an aggregated batch. The aggregated batch was then dried in an oven at 90° C. for 24 hours. The dried batch was manually forced through a 20 mesh screen. The screened material was then loosely packed in a 99.9% $Al_2O_3$ crucible and heat treated in an electric furnace to a temperature of 1650° C. The temperature schedule used for heating and subsequent cooling was:
1) increasing the temperature 3° C./min till reaching a temperature of 1650° C.,
2) maintaining the temperature at 1650° C. for 5 hours, and
3) decreasing the temperature 3° C./min till reaching room temperature.

Heat treated batch material (750 grams) as well as 250 ml of $H_2O$ and 2 grams of the dispersant, Darvan 821 A of R. T. Vanderbilts, were then placed in a 2 quart rubber lined ball mill and wet ground using a grinding media of 0.5 inch diameter, 96% alumina. The resultant particle size of the ground material was 90% less than 6 microns. The sized suspension was then drain slip cast in plaster molds to obtain a tube of about 18 cm in length and having outer and inner diameters of about 14 mm and 10 mm, respectively. The tube was dried at room temperature for 3 days. The dried tube was then heat treated using a temperature schedule of:
1) increasing the temperature 3° C./min till reaching a temperature of 1650° C.,
2) maintaining the temperature of 1650° C. for 1 hour, and
3) decreasing the temperature 3° C./min till reaching room temperature.

EXAMPLE 2

Fabrication of membrane tube of 5% yttria/alumina

The fabrication process was the same as that used and described above in Example 1, but now utilizing yttria in place of lanthanum oxide.

EXAMPLE 3

Fabrication of membrane tube of 5% baria/alumina

The fabrication process was the same as that used and described above in Example 1 but now utilizing baria in place of lanthanum oxide.

EXAMPLE 4

Fabrication of membrane tube of 5% yttria/alumina, with silver oxygen dissociation catalyst A membrane tube of 5% yttria/alumina, as in Example 2, was fabricated. The exterior surface of the tube was metallized with a silver nitrate in water solution, containing 2 wt. % $AgNO_3$. Such metallization was achieved by painting a relatively thin discontinuous film of the $AgNO_3$ solution on the surface so that the heated zone of the tube contained approximately 0.5 mg of Ag spread over 50 $cm^2$ of surface.

EXAMPLE 5

Fabrication of membrane tube of 5% baria/alumina, with silver oxygen dissociation catalyst A membrane tube of 5% baria/alumina, as in Example 3, was fabricated. The exterior surface of the tube was metallized with the solution of $AgNO_3$ coated thereon, as in Example 4.

EXAMPLE 6

Fabrication of membrane tube of 5% baria/alumina, with platinum oxygen dissociation catalyst A membrane tube of 5% baria/alumina, as in Example 3, was fabricated and the exterior surface of the tube was metallized with the solution of chloroplatinic acid in water, having a concentration of 0.2 wt. % Pt. Such metallization was achieved by painting a relatively thin discontinuous film of the Pt solution on the surface so that the heated zone of the tube contained approximately 0.1 mg of Pt spread over 50 cm² of surface.

EXAMPLES 7-12 and Comparative Example 1

In Examples 7-12, the structure of Examples 1 through 6, respectively, and in Comparative Example 1, the structure of a commercial quartz tube having a 12 cm long heated zone and having outer and inner diameters of 5 and 3 mm, respectively, were tested for the conversion of methane to higher molecular weight hydrocarbons.

For the testing, a simple flow unit was assembled and contained a cylinder of pure methane, a furnace to heat the reactants and house the selected membrane tube structure, a gas chromatograph to analyze the products and associated piping and connections.

To limit and reduce the amount of methane reactant relative to methane-contacting membrane surface area, a "deadman" rod (6 mm O.D.) made of quartz was positioned centrally down the inside of each membrane tube.

The unit was operated with the following conditions:
Temperature = 800° C.
$CH_4$ flow rate = 6 cc/min.
Length of heated zone of tube = 12 cm
Reaction volume = 5 cc
Contact Time = 50 sec (Note: For the quartz tube, the reaction volume was 2.5 cc, the contact time was 25 seconds and no deadman was used.)

The products of these Examples and Comparative Example 1 were analyzed and the results are provided in Table 1, below.

TABLE 1

| Examples | Tube Material | Product Analyses Moles/Mole of Feed × 10⁵ | | |
|---|---|---|---|---|
| | | $CO_2$ | $C_2H_4$ | $C_2H_6$ |
| CE1 | Quartz | — | — | — |
| E7 | 5% La/Al₂O₃ | tr | — | tr |
| E8 | 5% Y/Al₂O₃ | 8 | 6 | 8 |
| E9 | 5% Ba/Al₂O₃ | 4 | 4 | 8 |
| E10 | 5% Y/Al₂O₃ (Ag) | 4 | 4 | 8 |
| E11 | 5% Ba/Al₂O₃ (Ag) | 4 | 4 | 8 |
| E12 | 5% Ba/Al₂O₃ (Pt) | 2 | 20 | 8 | wherein:
CE = Comparative Example
E = Example
tr = trace amounts
hyphen, "-" = not detected

DISCUSSION OF RESULTS

At the reaction conditions used in the set of examples of Table 1, the reaction of methane generally requires the presence of a form of oxygen. With the use of the quartz tube of Comparative Example 1, no $CO_2$ or $C_{2+}$ hydrocarbon products were detected, indicating the absence of oxygen. In the examples utilizing membrane structures of the invention (i.e., alumina with an activator metal and, in the case of Examples 9, 10 and 11 an oxygen dissociation catalyst), the presence of carbon dioxide in the product show the presence of oxygen. Further, the presence of ethane and/or ethylene show that reactions, e.g., oxidative coupling of methane, are occurring. Those examples utilizing membranes having Y and Ba as activators resulted in dramatically higher amounts of carbon dioxide, ethane and ethylene being formed than did the lanthanum/alumina tube of Example 7. Also, there was a significant boost in activity in Example 12 (tube material—5% Ba/Al₂O₃(Pt)) over and above the non-platinum containing materials, indicating the desirability of the use of such an oxygen dissociation catalyst with the membrane. The results of those examples having a silver oxygen dissociation catalyst on the membrane (e.g., Examples 10 and 11) were similar to the results obtained using similar membrane materials with no oxygen dissociation catalyst. This is believed due to most if not all the silver volatilizing off of the membrane tube at these reaction conditions. Thus the use of such silver oxygen dissociation catalyst will likely be limited to lower temperature processing.

Comparative Example 2

Fabrication of quartz tube with platinum oxygen dissociation catalyst

A quartz tube, as used in Comparative Example 1 was used and the exterior surface of the tube was metallized with a solution of chloroplatinic acid in water, having a concentration of 0.2 wt. % Pt, as was done to the membrane tube in Example 6.

EXAMPLE 13

Fabrication of membrane tube of 5% lanthanum oxide/alumina with platinum oxygen dissociation catalyst A membrane tube of 5% lanthanum oxide/alumina, as in Example 1, was fabricated. The exterior surface of this tube was then metallized with a solution of chloroplatinic acid in water, having a concentration of 0.2 wt. % Pt, as was done to the membrane tube in Example 6.

EXAMPLE 14

Fabrication of membrane tube of 5% yttria/alumina, with platinum oxygen dissociation catalyst A membrane tube of 5% yttria/alumina, as in Example 2, was fabricated. The exterior surface of this tube was then metallized with a solution of chloroplatinic acid in water, having a concentration of 2 wt. % Pt, as was done to the membrane tube in Example 6.

EXAMPLE 15

The membrane surface previously metallized with the silver oxygen dissociation catalyst of the membrane tube used in Example 10 was sandblasted to ensure that none of the silver catalyst remained on the membrane. The thus conditioned membrane was then used, as described below, as a base case in the further testing.

EXAMPLES 16-21 and Comparative Examples 3-4

In Comparative Examples 3-4, the membrane structures of a quartz tube (as used in Comparative Example 1) and the membrane structure of Comparative Example 2, and in Examples 16-21, the membrane structures of Examples 1, 13, 15, 14, 3 and 6 respectively, were tested for the conversion of methane to higher molecular weight hydrocarbons, in the same manner as was done in Examples 7-12 and Comparative Example 1 but now using a smaller furnace resulting in a correspondingly smaller heated zone and correspondingly smaller reaction volume and reduced contact time.

The unit was operated with the following conditions:
Temperature = 800° C.
$CH_4$ flow rate = 6 cc/min.
Length of heated zone of tube = 4 cm
Reaction Volume = 1.6 cc
Contact Time = 15 sec (Note: For the quartz tube, the reaction volume was 0.8 cc, the contact time was 8 seconds and no deadman was used.)

The products of these examples and comparative examples were analyzed and the results are provided in Table 2, below.

TABLE 2

| Tube Material | Example | Product Analyses Moles/Mole of Feed × 10⁵ 800° C. | | | Example | Product Analyses Moles/Mole of Feed × 10⁵ 900° C. | | |
|---|---|---|---|---|---|---|---|---|
| | | $CO_2$ | $C_2H_4$ | $C_2H_6$ | | $CO_2$ | $C_2H_4$ | $C_2H_6$ |
| Quartz | CE3 | — | — | 2 | CE5 | — | — | 6 |
| Quartz (Pt) | CE4 | — | — | 2 | CE6 | — | — | 5 |
| 5% La/Al$_2$O$_3$ | E16 | — | — | 1 | E22 | — | 2 | 5 |
| 5% La/Al$_2$O$_3$ (Pt) | E17 | — | — | — | E23 | 1 | 2 | 5 |
| 5% Y/Al$_2$O$_3$ | E18 | 4 | — | 3 | E24 | 2 | 8 | 9 |
| 5% Y/Al$_2$O$_3$ (Pt) | E19 | 9 | — | 10 | E25 | 4 | 20 | 18 |
| 5% Ba/Al$_2$O$_3$ | E20 | — | — | 4 | E26 | — | 4 | 4 |
| 5% Ba/Al$_2$O$_3$ (Pt) | E21 | 9 | — | 2 | E27 | 4 | 25 | 18 |

Wherein:
CE = Comparative Example
E = Example
hyphen, "—" = not detected

DISCUSSION OF RESULTS

Quartz itself is an oxide. The product analyses of Comparative Examples 3 and 4 showed the formation of some $C_2H_6$ but no $CO_2$. It is believed that at these conditions and using a quartz tube, previously unseen background non-oxidative pyrolysis of methane is occurring. The belief is further supported by the product analyses of Comparative Examples 5 and 6 which show the formation of greater relative amounts of $C_2H_6$ at the higher reaction temperature of 900° C. and still no $CO_2$ in the product.

In Examples 15 and 16, membrane structures wherein lanthanum oxide was used as the activator metal realized little or no $CO_2$, $C_2H_4$ or $C_2H_6$ formation, similar to Comparative Examples 3 and 4. At 900° C., however, in addition to $C_2H_6$ formation, some formation of $C_2H_4$ and/or $CO_2$ is seen. It is theorized that at the higher operating temperatures used in Examples 21 and 22, at least some oxygen conveyance is being realized with the tested material, particularly with the material of Example 22 which contains the platinum oxygen dissociation catalyst, as seen through the presence of $CO_2$ in the product.

In Examples 17-20 and 23-26, greater relative amounts of products are obtained. Greater relative amounts of products are in particular obtained with the operation at the higher temperature of 900° C. and especially with the membrane structures having the platinum oxygen dissociation catalyst.

While not wishing to be bound by any theory or particular mode of operation, it is theorized that while it would normally be thought desirable to maintain the membrane as thin as possible while preserving sufficient physical integrity for practical operation, as larger flux of oxygen would typically be associated with shorter transport distances, these examples which show greater amounts of products being realized with those structures having platinum oxygen dissociation catalyst indicate that the interfacial transport mechanism might be the rate limiting factor and that the thickness of the membrane may be relatively immaterial regarding the rate of reaction of the flux rate of oxygen through the membrane thereby allowing the use of relatively thick membranes without detrimentally effecting the conveyance of oxygen.

The foregoing detailed description is given for clearness of understanding only, and no unnecessary limitations are to be understood therefrom, as modifications within the scope of the invention would be obvious to those skilled in the art.

Further, all disclosures of every application, patent, document and article identified herein above is specifically incorporated herein by reference.

That which is claimed is:

1. A method for the oxidative conversion of a gaseous hydrocarbon reactant, said method comprising the steps of:

contacting, at oxygen conveyance conditions, a first surface of a membrane with an oxygen-containing gas, said membrane being substantially impervious to non-oxygen gases and comprising an oxidative conversion contact material of a mixed oxide comprising a cationic species of aluminum and a cationic species of at least one multivalent activator metal and with said membrane permitting selective conveyance of a form of oxygen therethrough, and contacting, at reactive conditions and in the presence of oxygen conveyed by said membrane, a second surface of the membrane with a stream comprising at least one gaseous hydrocarbon reactant capable of reacting with oxygen to produce an oxidative conversion product.

2. The method of claim 1 wherein said first surface additionally comprises an oxygen dissociation catalyst.

3. The method of claim 2 wherein said oxygen dissociation catalyst comprises platinum.

4. The method of claim 1 wherein said hydrocarbon reactant comprises methane.

5. The method of claim 4 wherein said oxidative conversion product comprises at least one $C_{2+}$ hydrocarbon.

6. The method of claim 4 wherein said oxidative conversion product comprises carbon monoxide.

7. The method of claim 1 wherein said activator metal is selected from Groups 1, 2, 3 and 13 or the rare earth elements of the Periodic Table of Elements.

8. The method of claim 7 wherein said activator metal is yttrium.

9. The method of claim 7 wherein said activator metal is barium.

10. The method of claim 1 wherein said oxygen-containing gas additionally comprises at least one gaseous component in addition to free oxygen.

11. The method of claim 10 wherein said oxygen-containing gas comprises air.

12. The method of claim 1 wherein said mixed oxide comprises, on an oxygen-free basis, at least about 50 to 70 wt. % of a cationic species of aluminum and no more than about 1 to 30 wt. % of a cationic species of activator metal.

13. A method for the oxidative conversion of methane, said method comprising the steps of:
 contacting, at oxygen conveyance conditions, a first surface of a membrane with a first stream comprising free oxygen with said membrane being substantially impervious to non-oxygen gases and comprising an oxidative conversion contact material of a mixed oxide comprising, on an oxygen-free basis, at least about 50 to 70 wt. % of a cationic species of aluminum and no more than about 1 to 30 wt. % of a cationic species of at least one multivalent activator metal selected from Groups 1, 2, 3 or 13 or the rare earth elements of the Periodic Table of Elements with said membrane permitting selective conveyance of a form of oxygen therethrough, and
 contacting, at reactive conditions and in the presence of oxygen conveyed by said membrane, a second surface of the membrane with a second stream comprising methane to produce an oxidative conversion product.

14. The method of claim 13 wherein said oxidative conversion product comprises at least one $C_{2+}$ hydrocarbon.

15. The method of claim 13 wherein said oxidative conversion product comprises carbon monoxide.

16. The method of claim 13 wherein said activator metal is yttrium.

17. The method of claim 13 wherein said activator metal is barium.

18. The method of claim 13 wherein said first stream additionally comprises at least one gaseous component in addition to free oxygen.

19. The method of claim 13 wherein said first stream comprises air.

20. A method for the oxidative conversion of methane, said method comprising the steps of:
 contacting, at oxygen conveyance conditions, a first surface of a membrane with a first stream comprising air, said membrane being substantially impervious to non-oxygen gases and comprising an oxidative conversion contact material of a mixed oxide comprising, on an oxygen-free basis, at least about 50 to 70 wt. % of a cationic species of aluminum and no more than about 1 to 30 wt. % of a cationic species of at least one multivalent activator metal selected from the group consisting of yttrium and barium, said first surface also comprising an oxygen dissociation catalyst effective in effecting dissociation of oxygen and comprising at least one metal selected from the group consisting of palladium and platinum with said membrane permitting selective conveyance of a form of oxygen therethrough, and
 contacting, at reactive conditions and in the presence of oxygen conveyed by said membrane, a second surface of the membrane with a second stream comprising methane to produce an oxidative conversion product.

21. The method of claim 20 wherein said reactive conditions include a temperature of about 900° C. and said oxidative conversion products include ethane and ethylene.

22. The method of claim 20 wherein said oxidative conversion of methane comprises oxidative coupling of methane to form higher molecular weight hydrocarbons.

23. The method of claim 22 wherein said second surface of the membrane comprises an oxidative coupling contact material.

24. The method of claim 23 wherein said oxidative coupling contact material comprises Al.

* * * * *